US010688102B2

(12) United States Patent
Tabuteau

(10) Patent No.: US 10,688,102 B2
(45) Date of Patent: *Jun. 23, 2020

(54) COMBINATION TREATMENT FOR MIGRAINE AND OTHER PAIN

(71) Applicant: AXSOME THERAPEUTICS, INC., New York, NY (US)

(72) Inventor: Herriot Tabuteau, New York, NY (US)

(73) Assignee: AXSOME THERAPEUTICS, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/513,612

(22) Filed: Jul. 16, 2019

(65) Prior Publication Data

US 2019/0336510 A1 Nov. 7, 2019

Related U.S. Application Data

(63) Continuation-in-part of application No. PCT/US2018/032162, filed on May 10, 2018, which is a continuation-in-part of application No. PCT/US2018/012433, filed on Jan. 4, 2018.

(60) Provisional application No. 62/536,466, filed on Jul. 25, 2017, provisional application No. 62/526,884, filed on Jun. 29, 2017, provisional application No. 62/802,198, filed on Feb. 6, 2019, provisional application No. 62/803,756, filed on Feb. 11, 2019, provisional application No. 62/835,613, filed on Apr. 18, 2019, provisional application No. 62/846,311, filed on May 10, 2019.

(51) Int. Cl.
| | | |
|---|---|---|
| *A61K 31/5415* | (2006.01) | |
| *A61K 31/4196* | (2006.01) | |
| *A61K 9/20* | (2006.01) | |
| *A61K 31/4184* | (2006.01) | |
| *A61K 31/50* | (2006.01) | |
| *A61P 25/06* | (2006.01) | |

(52) U.S. Cl.
CPC .......... *A61K 31/5415* (2013.01); *A61K 9/205* (2013.01); *A61K 9/2013* (2013.01); *A61K 9/2086* (2013.01); *A61K 31/4184* (2013.01); *A61K 31/4196* (2013.01); *A61K 31/50* (2013.01); *A61P 25/06* (2018.01)

(58) Field of Classification Search
CPC ...... A61K 31/5415; A61K 31/50; A61P 25/06
USPC .......................................... 514/226.5, 252.01
See application file for complete search history.

(56) References Cited

U.S. PATENT DOCUMENTS

| | | | |
|---|---|---|---|
| 4,233,199 A | 11/1980 | Trummlitz et al. | |
| 4,233,299 A * | 11/1980 | Trummlitz | C07D 275/06 514/226.5 |
| 5,872,145 A | 2/1999 | Plachetka | |
| 6,060,499 A | 5/2000 | Plachetka | |
| 6,077,539 A | 6/2000 | Plachetka et al. | |
| 6,284,269 B1 | 9/2001 | Struengmann et al. | |
| 6,384,034 B2 * | 5/2002 | Simitchieva | A61K 31/42 514/252.01 |
| 6,479,551 B1 | 11/2002 | Plachetka et al. | |
| 6,495,535 B1 | 12/2002 | Plachetka et al. | |
| 6,586,458 B1 | 7/2003 | Plachetka | |
| 6,926,907 B2 | 8/2005 | Plachetka | |
| 7,030,162 B2 | 4/2006 | Plachetka et al. | |
| 7,060,694 B2 | 6/2006 | Plachetka et al. | |
| 7,332,183 B2 | 2/2008 | Plachetka et al. | |
| 8,022,095 B2 | 9/2011 | Plachetka | |
| 8,206,741 B2 | 6/2012 | Plachetka | |
| 8,512,727 B2 | 8/2013 | Cooper | |
| 8,557,285 B2 | 10/2013 | Plachetka | |
| 8,835,407 B2 | 9/2014 | Mosher et al. | |
| 8,852,636 B2 | 10/2014 | Plachetka | |
| 8,858,996 B2 | 10/2014 | Plachetka | |
| 8,865,190 B2 | 10/2014 | Plachetka | |
| 8,945,621 B2 | 2/2015 | Ault et al. | |
| 9,161,920 B2 | 10/2015 | Plachetka | |
| 9,198,888 B2 | 12/2015 | Plachetka | |
| 9,220,698 B2 | 12/2015 | Ault et al. | |
| 9,265,732 B2 | 2/2016 | Plachetka et al. | |
| 9,345,695 B2 | 5/2016 | Plachetka | |

(Continued)

FOREIGN PATENT DOCUMENTS

| | | |
|---|---|---|
| CA | 2565941 A1 | 11/2005 |
| CN | 101984960 A | 3/2011 |

(Continued)

OTHER PUBLICATIONS

Hu et al., Predicting Biological Functions of Compounds Based on Chemical-Chemical Interactions, PLoS One, 6(12), Dec. 2011, 9 pgs.
Johnell et al., Concomitant Use of Gastroprotective Drugs Among Elderly NSAID/COX-2 Selective Inhibitor Users: A Nationwide Register-Based Study, Clinical Drug Investigation, 28(11), 687-695, Nov. 2008.
Leonard et al., Proton Pump Inhibitors and Traditional Nonsteroidal Anti-Inflammatory Drugs and the Risk of Acute Interstitial Nephritis and Acute Kidney Injury, Pharmacoepidemiology and Drug Safety, 21(11), 1155-1172, Nov. 2012.

(Continued)

*Primary Examiner* — Kevin E Weddington
(74) *Attorney, Agent, or Firm* — Maschoff Brennan; Brent A. Johnson; Yuefen Zhou

(57) ABSTRACT

Disclosed herein are methods of treating pain, such as migraine, comprising administering meloxicam and rizatriptan to a human being suffering from pain, such as migraine. For migraine, these methods may be particularly useful when the meloxicam and rizatriptan are administered while the human being is suffering from an acute attack of migraine pain or migraine aura. In some embodiments, the combination of meloxicam and rizatriptan may be administered in a manner that results in a $T_{max}$ of meloxicam of 3 hours or less.

47 Claims, 1 Drawing Sheet

(56) References Cited

U.S. PATENT DOCUMENTS

| | | | |
|---|---|---|---|
| 9,364,439 B2 | 6/2016 | Plachetka | |
| 9,393,208 B2 | 7/2016 | Ault et al. | |
| 9,539,214 B2 | 1/2017 | Plachetka | |
| 9,707,181 B2 | 7/2017 | Plachetka | |
| 9,801,824 B2 | 10/2017 | Ault et al. | |
| 9,801,827 B2 | 10/2017 | Plachetka et al. | |
| 9,821,075 B2 | 11/2017 | Tabuteau | |
| 10,029,010 B1 | 7/2018 | Tabuteau | |
| 10,058,614 B2 | 8/2018 | Tabuteau | |
| 10,137,131 B2 * | 11/2018 | Tabuteau | A61K 9/2009 |
| 10,195,278 B2 | 2/2019 | Tabuteau | |
| 10,195,279 B2 | 2/2019 | Tabuteau | |
| 10,265,324 B2 | 4/2019 | Tabuteau | |
| 10,265,399 B2 | 4/2019 | Tabuteau | |
| 10,265,400 B2 | 4/2019 | Tabuteau | |
| 10,307,484 B2 | 6/2019 | Tabuteau | |
| 10,322,181 B2 | 6/2019 | Tabuteau | |
| 10,363,312 B2 | 7/2019 | Tabuteau | |
| 10,369,224 B2 | 8/2019 | Tabuteau | |
| 10,369,225 B2 | 8/2019 | Tabuteau | |
| 10,426,839 B2 | 10/2019 | Tabuteau | |
| 10,456,471 B2 | 10/2019 | Tabuteau | |
| 10,463,736 B2 | 11/2019 | Tabuteau | |
| 10,471,014 B2 | 11/2019 | Tabuteau | |
| 10,471,068 B2 | 11/2019 | Tabuteau | |
| 10,471,069 B2 | 11/2019 | Tabuteau | |
| 10,485,871 B2 | 11/2019 | Tabuteau | |
| 10,512,692 B2 | 12/2019 | Tabuteau | |
| 10,512,693 B2 | 12/2019 | Tabuteau | |
| 10,517,950 B1 | 12/2019 | Tabuteau | |
| 10,532,101 B1 | 1/2020 | Tabuteau | |
| 10,537,642 B1 | 1/2020 | Tabuteau | |
| 10,561,664 B1 | 2/2020 | Tabuteau | |
| 10,583,088 B2 | 3/2020 | Tabuteau | |
| 10,583,144 B2 | 3/2020 | Tabuteau | |
| 2002/0016348 A1 | 2/2002 | Simitchieva et al. | |
| 2004/0229038 A1 | 11/2004 | Cooper et al. | |
| 2005/0249806 A1 | 11/2005 | Proehl et al. | |
| 2007/0154542 A1 | 7/2007 | Tananbaum et al. | |
| 2007/0281927 A1 | 12/2007 | Tyavanagimatt et al. | |
| 2009/0068262 A1 | 3/2009 | Zalit et al. | |
| 2009/0203680 A1 | 8/2009 | Hanna | |
| 2010/0226943 A1 | 9/2010 | Brennan et al. | |
| 2013/0266658 A1 | 10/2013 | Weiß et al. | |
| 2016/0228576 A1 | 8/2016 | Tabuteau | |
| 2018/0050106 A1 | 2/2018 | Tabuteau | |
| 2018/0207274 A1 | 7/2018 | Tabuteau | |
| 2018/0214380 A1 | 8/2018 | Tabuteau | |
| 2018/0256593 A1 | 9/2018 | Tabuteau | |
| 2018/0264114 A1 | 9/2018 | Tabuteau | |
| 2018/0264115 A1 | 9/2018 | Tabuteau | |
| 2018/0271981 A1 | 9/2018 | Tabuteau | |
| 2018/0280306 A1 | 10/2018 | Tabuteau | |
| 2018/0280308 A1 | 10/2018 | Tabuteau | |
| 2018/0280512 A1 | 10/2018 | Tabuteau | |
| 2018/0289806 A1 | 10/2018 | Tabuteau | |
| 2018/0289807 A1 | 10/2018 | Tabuteau | |
| 2018/0289808 A1 | 10/2018 | Tabuteau | |
| 2019/0000975 A1 | 1/2019 | Tabuteau | |
| 2019/0070192 A1 | 3/2019 | Tabuteau | |
| 2019/0142942 A1 | 5/2019 | Tabuteau | |
| 2019/0142943 A1 | 5/2019 | Tabuteau | |
| 2019/0224320 A1 | 7/2019 | Tabuteau | |
| 2019/0224321 A1 | 7/2019 | Tabuteau | |
| 2019/0231792 A1 | 8/2019 | Tabuteau | |
| 2019/0255177 A1 | 8/2019 | Tabuteau | |
| 2019/0307884 A1 | 10/2019 | Tabuteau | |
| 2019/0314504 A1 | 10/2019 | Tabuteau | |
| 2019/0336510 A1 | 11/2019 | Tabuteau | |
| 2020/0030338 A1 | 1/2020 | Tabuteau | |
| 2020/0038408 A1 | 2/2020 | Tabuteau | |
| 2020/0085951 A1 | 3/2020 | Tabuteau | |
| 2020/0085952 A1 | 3/2020 | Tabuteau | |
| 2020/0085953 A1 | 3/2020 | Tabuteau | |
| 2020/0085954 A1 | 3/2020 | Tabuteau | |
| 2020/0085955 A1 | 3/2020 | Tabuteau | |

FOREIGN PATENT DOCUMENTS

| | | |
|---|---|---|
| CN | 101987081 | 3/2011 |
| CN | 102526058 A | 7/2012 |
| WO | 1998006392 A1 | 2/1998 |
| WO | 1999009988 A1 | 3/1999 |
| WO | 2000035448 | 6/2000 |
| WO | 2000059475 | 10/2000 |
| WO | 2005021041 A1 | 3/2005 |
| WO | 2005076987 | 8/2005 |
| WO | 2005105102 A1 | 11/2005 |
| WO | 2008006216 | 1/2008 |
| WO | 2012072570 | 6/2012 |
| WO | 2014161131 A1 | 10/2014 |
| WO | 2016131067 | 8/2016 |
| WO | 2017042607 | 3/2017 |
| WO | 2018129220 | 7/2018 |

OTHER PUBLICATIONS

Vonkeman et al., Proton-Pump Inhibitors are Associated with a Reduced Risk for Bleeding and Perforated Gastroduodenal Ulcers Attributable to Non-Steroidal Anti-Inflammatory Drugs: A Nested Case-Control Study, Arthritis Research & Therapy, 9(3), May 2007, 8 pgs.

Yilmaz et al., Does Adding Misoprostol to Standard Intravenous Proton Pump Inhibitor Protocol Improve the Outcome of Aspirin/NSAID-Induced Upper Gastrointestinal Bleeding?, Digestive Diseases and Sciences, 52(1), 110-118, Jan. 2007.

International search report dated Aug. 11, 2016, corresponding to international patent application No. PCT/US2016/026991.

Written opinion of the international searching authority dated Aug. 11, 2016, corresponding to international patent application No. PCT/US2016/026991.

Stella et al., Toxicologic Pathology, 2008, 36:30-42.

Jain et al., AAAPS PharmSciTech, 2011, 12(4):1163-1175.

Baboota et al., Journal of Inclusion Phenomena and Macrocyclic Chemistry, 2005, 51:219-224.

U.S. Appl. No. 15/132,130, filed Apr. 18, 2016 First Named Inventor: Herriot Tabuteau Assignee: Axsome Therapeutics, Inc.

U.S. Appl. No. 15/797,955, filed Oct. 30, 2017 First Named Inventor: Herriot Tabuteau Assignee: Axsome Therapeutics, Inc.

U.S. Appl. No. 15/902,770, filed Feb. 22, 2018 First Named Inventor: Herriot Tabuteau Assignee: Axsome Therapeutics, Inc.

U.S. Appl. No. 15/936,176, filed Mar. 26, 2018 First Named Inventor: Herriot Tabuteau Assignee: Axsome Therapeutics, Inc.

U.S. Appl. No. 15/976,800, filed May 10, 2018 First Named Inventor: Herriot Tabuteau Assignee: Axsome Therapeutics, Inc.

U.S. Appl. No. 15/984,055, filed May 18, 2018 First Named Inventor: Herriot Tabuteau Assignee: Axsome Therapeutics, Inc.

U.S. Appl. No. 15/986,215, filed May 22, 2018 First Named Inventor: Herriot Tabuteau Assignee: Axsome Therapeutics, Inc.

U.S. Appl. No. 15/988,104, filed May 24, 2018 First Named Inventor: Herriot Tabuteau Assignee: Axsome Therapeutics, Inc.

U.S. Appl. No. 15/989,734, filed May 25, 2018 First Named Inventor: Herriot Tabuteau Assignee: Axsome Therapeutics, Inc.

U.S. Appl. No. 16/000,701, filed Jun. 5, 2018 First Named Inventor: Herriot Tabuteau Assignee: Axsome Therapeutics, Inc.

U.S. Appl. No. 16/001,697, filed Jun. 6, 2018 First Named Inventor: Herriot Tabuteau Assignee: Axsome Therapeutics, Inc.

U.S. Appl. No. 16/002,865, filed Jun. 7, 2018 First Named Inventor: Herriot Tabuteau Assignee: Axsome Therapeutics, Inc.

U.S. Appl. No. 16/006,548, filed Jun. 12, 2018 First Named Inventor: Herriot Tabuteau Assignee: Axsome Therapeutics, Inc.

U.S. Appl. No. 16/006,642, filed Jun. 12, 2018 First Named Inventor: Herriot Tabuteau Assignee: Axsome Therapeutics, Inc.

U.S. Appl. No. 16/006,692, filed Jun. 12, 2018 First Named Inventor: Herriot Tabuteau Assignee: Axsome Therapeutics, Inc.

Hosie et al., British Journal of Rheumatology, 35 (suppl.1), 39-43, 1996.

(56) References Cited

OTHER PUBLICATIONS

Wojtulewski et al., British Journal of Rheumatology; 35 (suppl.1), 22-28,1996.
Goldstein et al., Intragastric Acid Control in Non-Steroidal Anti-inflammatory Drug Users: Comparison of Esomeprazole, Lansoprazole and Pantoprazole, Alimentary Pharmacology & Therapeutics 23, 1189-1196, 2006.
Euller-Ziegler et al. Meloxicam: a review of its pharmacokinetics, efficacy and tolerability following intramuscular administration, Inflamm. res. 50, Supplement 1, S5-S9, 2001.
U.S. Appl. No. 16/181,086, filed Nov. 5, 2018 First Named Inventor: Herriot Tabuteau Assignee: Axsome Therapeutics, Inc.
U.S. Appl. No. 16/247,406, filed Jan. 14, 2019 First Named Inventor: Herriot Tabuteau Assignee: Axsome Therapeutics, Inc.
U.S. Appl. No. 16/248,449, filed Jan. 15, 2019 First Named Inventor: Herriot Tabuteau Assignee: Axsome Therapeutics, Inc.
Iroko Pharmaceuticals, Vivlodex Label, Oct. 2015.
Mayo Clinic, http://web. archive.org/web/20141113013539/https://www.mayoclinic.org/drugs-supplements /meloxicam-oral-route/proper-use/drg-20066928 (2014) (retrievd from the internet Mar. 3, 2019) (Year: 2014).
U.S. Appl. No. 16/372,958, filed Apr. 2, 2019 First Named Inventor: Herriot Tabuteau Assignee: Axsome Therapeutics, Inc.
U.S. Appl. No. 16/372,977, filed Apr. 2, 2019 First Named Inventor: Herriot Tabuteau Assignee: Axsome Therapeutics, Inc.
U.S. Appl. No. 16/374,081, filed Apr. 3, 2019 First Named Inventor: Herriot Tabuteau Assignee: Axsome Therapeutics, Inc.
U.S. Appl. No. 16/403,034, filed May 3, 2019 First Named Inventor: Herriot Tabuteau Assignee: Axsome Therapeutics, Inc.
U.S. Appl. No. 16/440,695, filed Jun. 13, 2019 First Named Inventor: Herriot Tabuteau Assignee: Axsome Therapeutics, Inc.
U.S. Appl. No. 16/454,319, filed Jun. 27, 2019 First Named Inventor: Herriot Tabuteau Assignee: Axsome Therapeutics, Inc.
U.S. Appl. No. 16/513,612, filed Jul. 16, 2019 First Named Inventor: Herriot Tabuteau Assignee: Axsome Therapeutics, Inc.
Láinez, "Rizatriptan in the treatment of migraine." Neuropsychiatric disease and treatment, 2(3), p. 247, Sep. 2006.
U.S. Appl. No. 16/565,111, filed Sep. 9, 2019 First Named Inventor: Herriot Tabuteau Assignee: Axsome Therapeutics, Inc.
U.S. Appl. No. 16/566,476, filed Sep. 10, 2019 First Named Inventor: Herriot Tabuteau Assignee: Axsome Therapeutics, Inc.
U.S. Appl. No. 16/567,859, filed Sep. 11, 2019 First Named Inventor: Herriot Tabuteau Assignee: Axsome Therapeutics, Inc.
U.S. Appl. No. 16/568,703, filed Sep. 12, 2019 First Named Inventor: Herriot Tabuteau Assignee: Axsome Therapeutics, Inc.
U.S. Appl. No. 16/570,434, filed Sep. 13, 2019 First Named Inventor: Herriot Tabuteau Assignee: Axsome Therapeutics, Inc.
U.S. Appl. No. 16/570,451, filed Sep. 13, 2019 First Named Inventor: Herriot Tabuteau Assignee: Axsome Therapeutics, Inc.
U.S. Appl. No. 16/572,042, filed Sep. 16, 2019 First Named Inventor: Herriot Tabuteau Assignee: Axsome Therapeutics, Inc.
U.S. Appl. No. 16/589,692, filed Oct. 1, 2019 First Named Inventor: Herriot Tabuteau Assignee: Axsome Therapeutics, Inc.
U.S. Appl. No. 16/653,877, filed Oct. 15, 2019 First Named Inventor: Herriot Tabuteau Assignee: Axsome Therapeutics, Inc.
Landy S, Rice K, Lobo B. Central sensitisation and cutaneous allodynia in migraine. CNS drugs, 18(6), 337-42, May 2004.
U.S. Appl. No. 16/688,491, filed Nov. 19, 2019 First Named Inventor: Herriot Tabuteau Assignee: Axsome Therapeutics, Inc.
U.S. Appl. No. 16/689,970, filed Nov. 20, 2019 First Named Inventor: Herriot Tabuteau Assignee: Axsome Therapeutics, Inc.
U.S. Appl. No. 16/690,464, filed Nov. 21, 2019 First Named Inventor: Herriot Tabuteau Assignee: Axsome Therapeutics, Inc.
U.S. Appl. No. 16/693,052, filed Nov. 22, 2019 First Named Inventor: Herriot Tabuteau Assignee: Axsome Therapeutics, Inc.
U.S. Appl. No. 16/694,440, filed Nov. 25, 2019 First Named Inventor: Herriot Tabuteau Assignee: Axsome Therapeutics, Inc.
Weatherall, "Drug therapy in headache," Clin. Med. (Lond.), 15(3), 273-279, Jun. 2015. (PMID: 26031979, Year 2015).
U.S. Appl. No. 16/773,567, filed Jan. 27, 2020, First Named Inventor: Herriot Tabuteau, Assignee: Axsome Therapeutics, Inc.
U.S. Appl. No. 16/790,085, filed Feb. 13, 2020, First Named Inventor: Herriot Tabuteau, Assignee: Axsome Therapeutics, Inc.
Cameron C, et al., Triptans in the Acute Treatment of Migraine: A Systematic Review and Network Meta-Analysis, DOI: 10.1111/head.12601, https://www.ncbi.nlm.nih.gov/pubmed/26178694, accessed on Mar. 25, 2020.
Ng-Mak DS, et al., Acute migraine treatment with oral triptans and NSAIDs in a managed care population, DOI: 10.1111/j.1526-4610. 2007.01055.x, https://www.ncbi.nlm.nih.gov/pubmed/18819177, accessed on Mar. 25, 2020.
Lipton RB, et al., Impact of NSAID and Triptan use on developing chronic migraine: results from the American Migraine Prevalence and Prevention (AMPP) study, DOI: 10.1111/head.12201, https://www.ncbi.nlm.nih.gov/pubmed/23992516, accessed on Mar. 25, 2020.
U.S. Appl. No. 16/834,077, filed Mar. 30, 2020, First Named Inventor: Herriot Tabuteau, Assignee: Axsome Therapeutics, Inc.
U.S. Appl. No. 16/835,848, filed Mar. 31, 2020, First Named Inventor: Herriot Tabuteau, Assignee: Axsome Therapeutics, Inc.
U.S. Appl. No. 16/837,769, filed Apr. 1, 2020, First Named Inventor: Herriot Tabuteau, Assignee: Axsome Therapeutics, Inc.
U.S. Appl. No. 16/841,436, filed Apr. 6, 2020, First Named Inventor: Herriot Tabuteau, Assignee: Axsome Therapeutics, Inc.
U.S. Appl. No. 16/842,063, filed Apr. 7, 2020, First Named Inventor: Herriot Tabuteau, Assignee: Axsome Therapeutics, Inc.
U.S. Appl. No. 16/843,490, filed Apr. 8, 2020, First Named Inventor: Herriot Tabuteau, Assignee: Axsome Therapeutics, Inc.
U.S. Appl. No. 16/844,634, filed Apr. 9, 2020, First Named Inventor: Herriot Tabuteau, Assignee: Axsome Therapeutics, Inc.

* cited by examiner

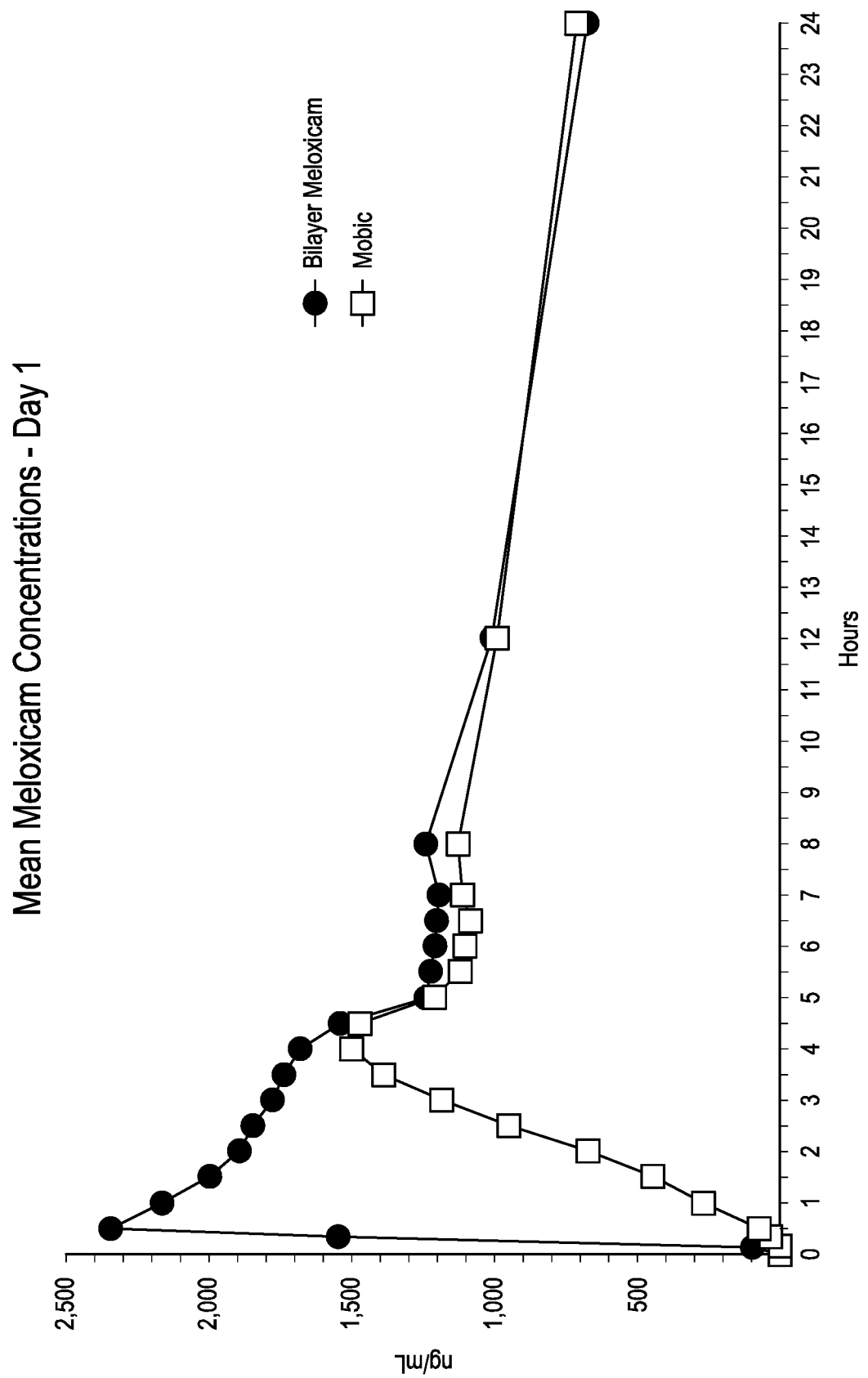

COMBINATION TREATMENT FOR MIGRAINE AND OTHER PAIN

CROSS-REFERENCE TO RELATED APPLICATIONS

This application is a continuation-in-part of PCT/US18/32162, filed May 10, 2018, which is continuation-in-part of PCT/US18/12433, filed Jan. 4, 2018; PCT/US18/32162 also claims benefit of U.S. Provisional Application Nos. 62/536,466, filed Jul. 25, 2017, 62/526,884, filed Jun. 29, 2017; this application also claims benefit of U.S. Provisional Application Nos. 62/802,198, filed Feb. 6, 2019, 62/803,756, filed Feb. 11, 2019, 62/835,613, filed Apr. 18, 2019, and 62/846,311, filed on May 10, 2019; all of which are incorporated by reference herein in their entirety.

BACKGROUND

There continues to be a need for therapies with improved efficacy in treating migraine and related conditions.

SUMMARY

Disclosed herein are methods of treating pain, such as migraine, comprising administering meloxicam and rizatriptan to a human being suffering from pain, such as migraine. For migraine, these methods may be particularly useful when the meloxicam and rizatriptan are administered while the human being is suffering from an acute attack of migraine pain or migraine aura. In some embodiments, about 8-13 mg of rizatriptan is administered to the human being. In some embodiments, the combination of meloxicam and rizatriptan (e.g. 8-13 mg of rizatriptan) may be administered in a manner that results in a $T_{max}$ of meloxicam of 3 hours or less, 2 hours or less, 110 minutes or less, and/or an $AUC_{0-24}$ of meloxicam of about 30-50 µg·hr/mL.

BRIEF DESCRIPTION OF THE DRAWINGS

FIG. 1 is a plot of meloxicam plasma concentration at various time points over the first 24 hours for an embodiment of a dosage form described herein and a commercially available meloxicam dosage form.

DETAILED DESCRIPTION

A combination of rizatriptan and meloxicam (referred to herein for convenience as a "subject combination") may be used to treat a variety of pain conditions.

Rizatriptan has the structure as shown below.

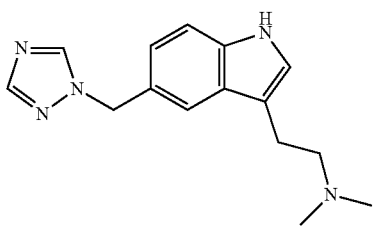

Rizatriptan

Meloxicam has the structure:

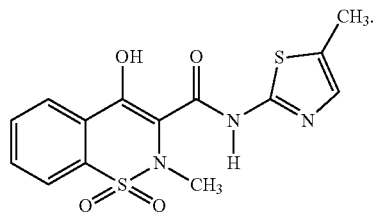 [SMILES: Cc1cnc(NC(=O)C2=C(O)c3ccccc3S(=O)(=O)N2C)s1]

Meloxicam exhibits anti-inflammatory, analgesic, and antipyretic activities. The meloxicam mechanism of action may be related to the inhibition of prostaglandin synthetase (cyclo-oxygenase, COX) which is involved in the initial steps of the arachidonic acid cascade, resulting in the reduced formation of prostaglandins, thromboxanes and prostacylin.

Unless otherwise indicated, any reference to a compound herein, such as meloxicam or rizatriptan, by structure, name, or any other means, includes pharmaceutically acceptable salts, alternate solid forms, such as polymorphs, solvates, hydrates, enantiomers, tautomers, deuterium-modified forms, or any other chemical species, such as precursors, prodrugs, or any other chemical species that may rapidly convert to a compound described herein under conditions in which the compounds are used as described herein.

A subject combination may be given enterally including, but not limited to, oral, sublingual, or rectal delivery, or parenterally including, but not limited to, intravenous, intramuscular, intranasal, or subcutaneous delivery. In some embodiments, both meloxicam and rizatriptan are administered orally. In some embodiments, meloxicam is administered intravenously and rizatriptan is administered orally. In some embodiments, meloxicam is administered intramuscularly and rizatriptan is administered orally.

Normally, the combination of meloxicam and rizatriptan is administered so that the human being receives the meloxicam and rizatriptan within a short period of time with respect to one another. For example, the meloxicam and rizatriptan may be administered within about 2 hours, within about 1 hour, within about 30 minutes, within about 20 minutes, within about 15 minutes, within about 10 minutes, within about 5 minutes, or within about 1 minute of one another. In some embodiments, the meloxicam and rizatriptan are administered simultaneously, which for the purpose of this disclosure includes administration within about 5 minutes. In some embodiments, the meloxicam and rizatriptan are administered in a single dosage form.

The term "treating" or "treatment" broadly includes any kind of treatment activity, including the diagnosis, cure, mitigation, or prevention of disease in man or other animals, or any activity that otherwise affects the structure or any function of the body of man or other animals.

A subject combination may be used to treat, or provide relief of, any type of pain including, but not limited to, migraine and other types of headache, inflammatory pain, musculoskeletal pain, neuropathic pain, chronic pain, acute pain, localized pain, systemic pain, cancer-related pain, acute pain, pain due to injury, pain due to illness (e.g., fever), post-operative pain, etc. In some instances, pain relief may be palliative, or pain relief may be provided independent of improvement of the disease or condition or the underlying cause of the disease or condition. For example, although the underlying disease may not improve, or may continue to progress, an individual suffering from the disease may experience pain relief. In some embodiments, the pain affects a muscle, nerve, cartilage, bone, ligament, tendon, tendon sheaths, bursae, or joint.

Migraine is a headache disorder characterized by recurrent headaches that may be moderate to severe. The headaches may affect one half of the head, may be pulsating in nature, and may last from 2 to 72 hours. Associated symptoms may include nausea, vomiting, and sensitivity to light (photophobia), sound (phonophobia), or smell. The pain can be made worse by physical activity. Migraines may be associated with an aura, which may be a short period of visual disturbance which signals that the headache will soon occur.

Administering a subject combination to a human being suffering from migraine, such as an acute attack of migraine pain or aura, may quickly result in a reduction in a migraine symptom, such as pain, nausea, vomiting, photophobia, or phonophobia, such as at or within about 5 minutes (intended as a shorthand for "at about 5 minutes, or within about 5 minutes"), at or within about 10 minutes, at or within about 30 minutes, at or within about 1 hour, at or within about 90 minutes, at or within about 2 hours, at or within about 2.5 hours, or at or within about 3 hours. In some embodiments, a human being experiences a reduction of, or complete relief from, pain, such as headache pain or migraine pain, nausea, vomiting, photophobia, and/or phonophobia, at or within about 1 hour, at or within about 90 minutes, at or within about 2 hours, at or within about 2.5 hours, or at or within about 3 hours. In some embodiments, the relief experienced, is greater than would be experienced by receiving the same amount of rizatriptan without meloxicam. In some embodiments, the relief experienced, is greater than would be experienced by receiving the same amount of meloxicam without rizatriptan.

Observation of relief or reduction in a symptom at a specific period of time, such as "at 2 hours," is useful because it allows the effectiveness of the treatment to be evaluated at a specific or consistent time point, which facilitates comparison between patients. Observation of relief or reduction in a symptom within a specific period of time, such as "within about 2 hours," is useful because it is desirable for relief or reduction of a symptom to occur as early as possible, and specifying that relief occur within a specified time sets a guideline in which it is desirable that relief occur.

For some methods, administration of the subject combination may achieve a reduction in migraine pain, nausea, vomiting, photophobia, or phonophobia that lasts at least about one hour, at least about two hours, at least about three hours, at least about four hours, at least about six hours, at least about eight hours, about 8-24 hours, about 24 hours, or more than 24 hours.

In some embodiments, the meloxicam and the rizatriptan are administered simultaneously (e.g. in a single dosage form, such as a single oral dosage form), and two hours after the meloxicam and the rizatriptan are administered, the human being experiences greater pain relief than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater pain relief than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater pain relief than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater pain relief than the human being would have experienced twenty-four hours after receiving the same amount of rizatriptan without the meloxicam.

In some embodiments, the meloxicam and the rizatriptan are administered simultaneously (e.g. in a single dosage form, such as a single oral dosage form), and two hours after the meloxicam and the rizatriptan are administered, the human being experiences greater relief from nausea than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from nausea than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from nausea than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from nausea than the human being would have experienced twenty-four hours after receiving the same amount of rizatriptan without the meloxicam.

In some embodiments, the meloxicam and the rizatriptan are administered simultaneously (e.g. in a single dosage form, such as a single oral dosage form), and two hours after the meloxicam and the rizatriptan are administered, the human being experiences greater relief from vomiting than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from vomiting than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from vomiting than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from vomiting than the human being would have experienced twenty-four hours after receiving the same amount of rizatriptan without the meloxicam. In some embodiments, the meloxicam and the rizatriptan are administered simultaneously (e.g. in a single dosage form, such as a single oral dosage form), and two hours after the meloxicam and the rizatriptan are administered, the human being experiences greater relief from photophobia than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from photophobia than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from photophobia than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from photophobia than the human being would have experienced twenty-four hours after receiving the same amount of rizatriptan without the meloxicam.

In some embodiments, the meloxicam and the rizatriptan are administered simultaneously (e.g. in a single dosage form, such as a single oral dosage form), and two hours after the meloxicam and the rizatriptan are administered, the human being experiences greater relief from phonophobia than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from phonophobia than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from phonophobia than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from phonophobia than the human being would have experienced twenty-four hours after receiving the same amount of rizatriptan without the meloxicam.

In some embodiments, the human being receiving the subject combination has a history of inadequate response to prior migraine treatments. For example, if the human being is asked whether he or she was pain-free within two hours of treatment for most attacks, and given the option of answering "never," "rarely," "less than half the time," or "half the time or more;" and the human being answers "never," "rarely," or "less than half the time," then the human being has had an inadequate response to the treatment. Similarly, if the human being is asked whether one dose of medication usually relieved the human being's headache and kept it away for at least 24 hours, and given the option of answering "never," "rarely," "less than half the time," or "half the time or more;" and the human being answers "never," "rarely," or "less than half the time," then the human being has had an inadequate response to the treatment.

In some embodiments, the human being receiving the subject combination has indicated that he or she was "never" pain-free within two hours of treatment for most attacks. In some embodiments, the human being receiving the subject combination has indicated that he or she was "rarely" pain-free within two hours of treatment for most attacks. In some embodiments, the human being receiving the subject combination has indicated that he or she was pain-free within two hours of treatment for most attacks "less than half the time."

In some embodiments, the human being receiving the subject combination has indicated that one dose of medication "never" relieved the respondent's headache and kept it away for at least 24 hours. In some embodiments, the human being receiving the subject combination has indicated that one dose of medication "rarely" relieved the respondent's headache and kept it away for at least 24 hours. In some embodiments, the human being receiving the subject combination has indicated that one dose of medication relieved the respondent's headache and kept it away for at least 24 hours "less than half the time."

In some methods, the subject combination may be administered to relieve inflammatory pain, including inflammatory musculoskeletal pain, pain due to injury, arthritis pain, and complex regional pain syndrome. In other embodiments, the inflammatory pain may be chronic or acute.

In some embodiments, the subject combination may be administered to relieve arthritis pain, or other signs and/or symptoms of arthritis. Arthritis refers to inflammatory joint diseases that can be associated with pain. Examples of arthritis include, but are not limited to, rheumatoid arthritis, juvenile rheumatoid arthritis (pauciarticular and polyarticular course), osteoarthritis, erosive osteoarthritis, sero-negative (non-rheumatoid), arthropathies, non-articular rheumatism, peri-articular disorders, axial spondyloarthritis, transient osteoarthritis of the hip, vertebral crush fractures, arthritis associated with osteoporosis, and neuropathic arthropathies including Charcot's foot, axial spondyloarthritis including ankylosing spondylitis, and SAPHO syndrome. In other embodiments, the arthritis pain may be chronic or acute. In some embodiments the subject combination may be administered to relief the signs and/or symptoms of an arthritis including but not limited to osteoarthritis.

In some embodiments, the subject combination may be administered to relieve neuropathic pain, including diabetic peripheral neuropathy, post-herpetic neuralgia, trigeminal neuralgia, monoradiculopathies, phantom limb pain, sciatica, pudendal neuralgia, and central pain. Other causes of neuropathic pain may include, but are not limited to, cancer-related pain, lumbar nerve root compression, spinal cord injury, post-stroke pain, central multiple sclerosis pain, HIV-associated neuropathy, and radio-therapy or chemo-therapy associated neuropathy. The neuropathic pain may be chronic or acute.

For some methods, the subject combination may be administered to relieve musculoskeletal pain. Examples of musculoskeletal pain may include, but are not limited to, back pain, low back pain (e.g., lumbosacral pain), neck pain, infection, cramps, tendonitis, epidondylitis, carpal tunnel syndrome, joint pain, fibromyalgia, pain due to injury, Tunnel syndromes, pain associated with bone fractures, sprains, fibrous dysplasia, osteogenesis imperfecta, Paget's disease of bone, transient osteoporosis, and transient osteoporosis of the hip. In other embodiments, the musculoskeletal pain may be chronic or acute.

For some methods, administration of the subject combination may achieve a reduction in pain that lasts at least about one hour, at least about two hours, at least about three hours, at least about four hours, at least about six hours, at least about eight hours, about 8 to about 24 hours, or about 24 hours. In other embodiments, administration of the subject combination may achieve a reduction in pain that is observed at about 10 minutes, at about 30 minutes, at about one hour, at about two hours, at about three hours, at about four hours, at about five hours, at about six hours, at or within about 5 minutes, at or within about 10 minutes, at or within about 15 minutes, at or within about 20 minutes, at or within about 25 minutes, at or within about 30 minutes, at or within about 35 minutes, at or within about 40 minutes, at or within about 45 minutes, at or within about 50 minutes, or at or within about 60 minutes, at two hours or less, at three hours or less, or other time period bound by these ranges, after administration of the subject combination.

A human being that is treated for a disease or condition, such as migraine, with a subject combination may be of any age. For example the person may have an age of about 0.1-10 years, about 10-90 years, about 20-80 years, about 30-75 years, about 40-70 years, about 1-16 years, about 80-95 years, about 18 years or more, about 20 years or more, about 25 years or more, about 30 years or more, about 40 years or more, about 45 years or more, about 50 years or more, about 55 years or more, about 60 years or more, about 65 years or more, or any other age in a range bounded by, or between, any of these values.

In some embodiments, a human being that is treated for a disease or condition, such as migraine, with a subject combination has suffered from the condition for at least 1 day, at least one week, at least 2 weeks, at least 1 month, at least 6 weeks, at least 2 months, at least 3 months, at least 6 months, at least 1 year, at least 5 years, at least 10 years, at least 15 years, at least 20 years, at least 30 years, at least 40 years, at least 50 years or any duration in a range bounded by, or between, any of these values.

In some embodiments, use of a cyclodextrin or a bicarbonate in a dosage form comprising the subject combination may improve the solubility or oral bioavailability (e.g. a higher $C_{max}$ and/or higher AUC) of meloxicam in a subject (human or animal) by at least about 10%, at least about 20%, at least about 30%, at least about 40%, at least about 50%, at least about 60%, at least about 70%, at least about 80%, at least about 90%, up to about 100%, up to about 200%, or any amount in a range bounded by, or between, any of these values as compared to administration of meloxicam alone.

In some embodiments, use of a cyclodextrin or a bicarbonate used in the subject combination may improve the solubility or oral bioavailability (e.g. a higher $C_{max}$ and/or higher AUC) of rizatriptan in a subject (human or animal) by at least about 10%, at least about 20%, at least about 30%, at least about 40%, at least about 50%, at least about 60%, at least about 70%, at least about 80%, at least about 90%, up to about 100%, up to about 200%, or any amount in a range bounded by, or between, any of these values as compared to administration of the rizatriptan alone.

In some embodiments, a dosage form used in the subject combination, including an oral, intravenous, or intramuscular dosage form, may contain meloxicam in an amount of about 1-50 mg; about 1-10 mg; about 1-5 mg; about 10-40 mg; about 1-35 mg; about 2-6 mg, about 3-7 mg, about 4-8 mg, about 5-10 mg, about 7-12 mg, about 5-15 mg, about 10-20 mg, about 10-30 mg, about 18-22 mg, about 19-21 mg, about 15-25 mg, about 20-30 mg, about 25-35 mg, about 30-40 mg, about 35-45 mg, about 40-50 mg, about 1-25 mg; about 1-15 mg; about 5-20 mg; about 5 mg; about 7.5 mg; about 10 mg; about 15 mg; about 20 mg; about 30 mg; or any amount in a range bounded by, or between, any of these values. For any amounts of meloxicam (or any other compound) described herein, salt forms of meloxicam (or another compound) may be present in the amounts recited above, or amounts that are molar equivalents to these amounts for the non-salt form of meloxicam (or another compound). These doses may be safe for repeated administration, such as 1, 2, 3, or 4 times a day, or may be repeated at an interval of about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 1-2 months, about 4 weeks, about 6 weeks, about 4-6 weeks, about 2-3 months, about 3-4 months, about 4-5 months, about 5-6 months, about 6-7 months, about 7-8 months, about 8-9 months, about 9-10 months, about 10-11 months, about 11-12 months, about 1-2 years, about 2 years, etc.

In some embodiments; a dosage form comprising the subject combination may contain rizatriptan in an amount of about 1-50 mg; about 1-10 mg; about 10-20 mg; about 20-30 mg; about 30-40 mg; or about 40-50 mg; about 10-40 mg; about 1-35 mg; about 1-25 mg; about 1-15 mg; about 1-10 mg; about 5-20 mg; about 1-5 mg; about 2-6 mg; about 3-7 mg; about 4-8 mg; about 5-10 mg; about 6-11 mg; about 7-12 mg; about 8-13 mg; about 9-11 mg; about 9-14 mg; about 10-15 mg; about 11-16 mg; about 12-17 mg; about 13-18 mg; about 14-19 mg; about 15-20 mg; about 5-15 mg; about 0.5 mg; about 1 mg; about 1.5 mg; about 2 mg; about 2.5 mg; about 3 mg; about 3.5 mg; about 4 mg; about 4.5 mg; about 5 mg; about 6 mg; about 7 mg; about 7.5 mg; about 8 mg, about 9 mg, about 10 mg; about 15 mg; about 20 mg, about 25 mg, about 30 mg; or any amount in a range bounded by, or between, any of these values.

For acute migraines, the amount of meloxicam and/or rizatriptan in a single dose, or the AUC of the meloxicam and/or rizatriptan associated with a single dose, is of particular interest. For example, after a single dose, the symptoms may be relieved for an extended period of time, such that, in the short term, repeated doses may not be needed. For more continuous conditions, including more chronic, continuous, or frequent migraine symptoms, daily, weekly, or monthly doses may be of particular interest.

For any amounts of rizatriptan described herein, salt forms of rizatriptan may be present in the amounts recited above, or amounts that are molar equivalents to these amounts for the rizatriptan free base. For example, assuming that the molecular weight of rizatriptan free base is 269.3 g/mol, 10 mg of rizatriptan is 37.1 mmol of rizatriptan. Thus, a molar equivalent of 10 mg of rizatriptan free base would be the mass of 37.1 mmol of that salt form. For example, for the benzoate salt (mw=391.2 g/mol), the molar equivalent of 10 mg of the free base (or 37.1 mmol), would be 14.5 mg. These doses may be safe for repeated administration, such as 1, 2, 3, or 4 times a day, or repeated at an interval of 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 4 weeks, 4-6 weeks, about 1-2 months, about 6 weeks, about 2-3 months, about 3-4 months, about 4-5 months, about 5-6 months, about 6-7 months, about 7-8 months, about 8-9 months, about 9-10 months, about 10-11 months, about 11-12 months, etc.

For some dosage forms, a cyclodextrin (such as SBEβCD) may be present in an amount of about 1-200 mg; about 1-100 mg; about 25-175 mg; about 50-150 mg; about 50-100 mg; about 50-200 mg; about 25-100 mg; about 75-150 mg; about 100-175 mg; about 20-80 mg; about 25-50 mg; about 60-100 mg; about 80-100 mg; about 100 mg; about 80-120 mg; about 100-120 mg; about 100-140 mg; about 120-160 mg; about 140-180 mg; about 150-200 mg, about 100-150 mg; about 30-90 mg; about 40-60 mg; about 40-80 mg; about 50-70 mg, about 55-65 mg, about 60-62 mg, or any amount in a range bounded by, or between, any of these values. A cyclodextrin may be effective in decreasing $T_{max}$ and/or increasing AUC of meloxicam and/or rizatriptan.

For some dosage forms, an inclusion complex of a drug (such as meloxicam or rizatriptan) and cyclodextrin is about 1-10%, about 5-20%, about 5-15%, about 6-16%, about 7-17%, about 8-18%, about 9-19%, about 10-20%, about 15-30%, about 30-40%, about 40-50%, about 50-70%, or about 70-90% of the total weight of the dosage form, or any percentage in a range bounded by any of these values.

Some dosage forms contain a bicarbonate (e.g., sodium bicarbonate) in amount of about 1-2000 mg; about 1-1000 mg; about 100-1000 mg; about 200-800 mg; about 1-500 mg; about 1-200 mg; about 1400 mg; about 50-750 mg; about 500-1000 mg; about 100-500 mg; about 100-300 mg; about 500-1000 mg; about 300-700 mg; about 400-600 mg; about 50-250 mg; about 50-100 mg; about 250-750 mg; about 100-200 mg; about 200-300 mg; about 300-400 mg; about 400-500 mg; about 410-510 mg; about 420-520 mg; about 430-530 mg; about 440-540 mg; about 450-550 mg; about 460-560 mg; about 470-570 mg; about 480-580 mg; about 490-590 mg; about 500-600 mg; about 600-700 mg; about 700-800 mg; about 800-900 mg; about 900-1,000 mg; about 150-650 mg; about 350-850 mg; about 400 mg; about 450 mg; about 500 mg, about 550 mg; about 600 mg; or any amount in a range bounded by, or between, any of these values.

A bicarbonate, such as sodium bicarbonate, may be at least about 10%, at least about 15%, at least about 20%, about 20-40%, about 30-50%, about 40-60%, about 50-70%, about 60-80%, or about 70-90%, or any percentage in a range bounded by any of these values, of the total weight of the dosage form.

In some embodiments, the daily dose of meloxicam, or the amount of meloxicam administered in a single day (either in one administration, or by two or more divided doses adding up to the daily dose) is about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 2-45 mg, about 2-50 mg, about 2-55 mg, about 2-60 mg, about 2-65 mg, about 2-70 mg, about 2-75 mg, about 3-8 mg, about 4-9 mg, about 5-10 mg, about 6-11 mg, about 7-12 mg, about 8-13 mg, about 9-14 mg, about 10-15 mg, about 11-16 mg, about 12-17 mg, about 13-18 mg, about 14-19 mg, about 15-20 mg, about 16-21 mg, about 17-22 mg, about 18-23 mg, about 19-24 mg, about 20-25 mg, about 21-26 mg, about 22-27 mg, about 23-28 mg, about 24-29 mg, about 25-30 mg, about 26-31 mg, about 27-32 mg, about 28-33 mg, about 29-34 mg, about 30-35 mg, about 31-36 mg, about 32-37 mg, about 33-38 mg, about 34-39 mg, about 35-40 mg, about 36-41 mg, about 37-42 mg, about 38-43 mg, about 39-44 mg, about 40-45 mg, about 41-46 mg, about 42-47 mg, about 43-48 mg, about 44-49 mg, about 45-50 mg, about 46-51 mg, about 47-52 mg, about 48-53 mg, about 49-54 mg, about 50-55 mg, about 51-56 mg, about 52-57 mg, about 53-58 mg, about 54-59 mg, about 55-60 mg, about 56-61 mg, about 57-62 mg, about 58-63 mg, about 59-64 mg, about 60-65 mg, about 61-66 mg, about 62-67 mg, about 63-68 mg, about 64-69 mg, about 65-70 mg, about 66-71 mg, about 67-72 mg, about 68-73 mg, about 69-74 mg, about 70-75 mg, or any amount in a range bounded by any of these values. The daily dose may be given as a single dose, given once a day, or may be given in 2, 3, 4, or more divided doses during a day.

In some embodiments, the weekly dose of meloxicam or the amount of meloxicam administered in a week (either in one administration, or by two or more divided doses adding up to the weekly dose) is about 1-1000 mg; about 1-500 mg; about 10-250 mg; about 100-300 mg; about 10-100 mg; about 10-150 mg; about 10-300 mg; about 20-150 mg; about 20-60 mg; about 30-70 mg; about 40-60 mg; about 50-70 mg; about 70-90 mg; about 90-110 mg; about 80-450 mg; about 80-100 mg; about 90-110 mg; about 100420 mg; about 110430 mg; about 120-140 mg; about 130-150 mg; about 140-160 mg; about 150470 mg; about 160-180 mg; about 170-190 mg; about 180-200 mg; about 190-210 mg; about 200-220 mg; about 210-230 mg; about 220-240 mg; about 230-250 mg; about 240-260 mg; about 250-270 mg; about 260-280 mg; about 270-290 mg; about 280-300 mg; about 290-310 mg; about 300-320 mg; about 310-330 mg; about 320-340 mg; about 330-350 mg; about 340-360 mg; about 350-370 mg; about 360-380 mg; about 370-390 mg; about 380-400 mg; about 390-410 mg; about 400-420 mg; about 410-430 mg; about 420-440 mg; about 430-450 mg; about 50 mg; about 55 mg; about 100-150 mg; about 30-100 mg; or any amount in a range bounded by, or between, any of these values. The weekly dose may be given as a single dose, given once a week, or may be given in 2, 3, 4, 5, 6, or 7 individual doses during a week.

In some embodiments, the monthly dose of meloxicam (e.g., an oral dose), or a dose administered over a period of a month, is about 5000 mg or less; about 4000 mg or less;

about 3000 mg or less; about 2000 mg or less; about 1000 mg or less; about 700 mg or less; about 600 mg or less; about 300-2400 mg; about 300-350 mg; about 310-360 mg; about 320-370 mg; about 330-380 mg; about 340-390 mg; about 350-400 mg; about 360-410 mg; about 370-420 mg; about 380-430 mg; about 390-440 mg; about 400-450 mg; about 410-460 mg; about 420-470 mg; about 430-480 mg; about 440-490 mg; about 450-500 mg; about 460-510 mg; about 470-520 mg; about 480-530 mg; about 490-540 mg; about 500-550 mg; about 510-560 mg; about 520-570 mg; about 530-580 mg; about 540-590 mg; about 550-600 mg; about 560-610 mg; about 570-620 mg; about 580-630 mg; about 590-640 mg; about 600-650 mg; about 610-660 mg; about 620-670 mg; about 630-680 mg; about 640-690 mg; about 650-700 mg; about 660-710 mg; about 670-720 mg; about 680-730 mg; about 690-740 mg; about 700-750 mg; about 710-760 mg; about 720-770 mg; about 730-780 mg; about 740-790 mg; about 750-800 mg; about 760-810 mg; about 770-820 mg; about 780-830 mg; about 790-840 mg; about 800-850 mg; about 810-860 mg; about 820-870 mg; about 830-880 mg; about 840-890 mg; about 850-900 mg; about 860-910 mg; about 870-920 mg; about 880-930 mg; about 890-940 mg; about 900-950 mg; about 910-960 mg; about 920-970 mg; about 930-980 mg; about 940-990 mg; about 950-1000 mg; about 960-1010 mg; about 970-1020 mg; about 980-1030 mg; about 990-1040 mg; about 1000-1050 mg; about 1010-1060 mg; about 1020-1070 mg; about 1030-1080 mg; about 1040-1090 mg; about 1050-1100 mg; about 1060-1110 mg; about 1070-1120 mg; about 1080-1130 mg; about 1090-1140 mg; about 1100-1150 mg; about 1110-1160 mg; about 1120-1170 mg; about 1130-1180 mg; about 1140-1190 mg; about 1150-1200 mg; about 1160-1210 mg; about 1170-1220 mg; about 1180-1230 mg; about 1190-1240 mg; about 1200-1250 mg; about 1210-1260 mg; about 1220-1270 mg; about 1230-1280 mg; about 1240-1290 mg; about 1250-1300 mg; about 1260-1310 mg; about 1270-1320 mg; about 1280-1330 mg; about 1290-1340 mg; about 1300-1350 mg; about 1310-1360 mg; about 1320-1370 mg; about 1330-1380 mg; about 1340-1390 mg; about 1350-1400 mg; about 1360-1410 mg; about 1370-1420 mg; about 1380-1430 mg; about 1390-1440 mg; about 1400-1450 mg; about 1410-1460 mg; about 1420-1470 mg; about 1430-1480 mg; about 1440-1490 mg; about 1450-1500 mg; about 1460-1510 mg; about 1470-1520 mg; about 1480-1530 mg; about 1490-1540 mg; about 1500-1550 mg; about 1510-1560 mg; about 1520-1570 mg; about 1530-1580 mg; about 1540-1590 mg; about 1550-1600 mg; about 1560-1610 mg; about 1570-1620 mg; about 1580-1630 mg; about 1590-1640 mg; about 1600-1650 mg; about 1610-1660 mg; about 1620-1670 mg; about 1630-1680 mg; about 1640-1690 mg; about 1650-1700 mg; about 1660-1710 mg; about 1670-1720 mg; about 1680-1730 mg; about 1690-1740 mg; about 1700-1750 mg; about 1710-1760 mg; about 1720-1770 mg; about 1730-1780 mg; about 1740-1790 mg; about 1750-1800 mg; about 1760-1810 mg; about 1770-1820 mg; about 1780-1830 mg; about 1790-1840 mg; about 1800-1850 mg; about 1810-1860 mg; about 1820-1870 mg; about 1830-1880 mg; about 1840-1890 mg; about 1850-1900 mg; about 1860-1910 mg; about 1870-1920 mg; about 1880-1930 mg; about 1890-1940 mg; about 1900-1950 mg; about 1910-1960 mg; about 1920-1970 mg; about 1930-1980 mg; about 1940-1990 mg; about 1950-2000 mg; about 1960-2010 mg; about 1970-2020 mg; about 1980-2030 mg; about 1990-2040 mg; about 2000-2050 mg; about 2010-2060 mg; about 2020-2070 mg; about 2030-2080 mg; about 2040-2090 mg; about 2050-2100 mg; about 2060-2110 mg; about 2070-2120 mg; about 2080-2130 mg; about 2090-2140 mg; about 2100-2150 mg; about 2110-2160 mg; about 2120-2170 mg; about 2130-2180 mg; about 2140-2190 mg; about 2150-2200 mg; about 2160-2210 mg; about 2170-2220 mg; about 2180-2230 mg; about 2190-2240 mg; about 2200-2250 mg; about 2210-2260 mg; about 2220-2270 mg; about 2230-2280 mg; about 2240-2290 mg; about 2250-2300 mg; about 2260-2310 mg; about 2270-2320 mg; about 2280-2330 mg; about 2290-2340 mg; about 2300-2350 mg; about 2310-2360 mg; about 2320-2370 mg; about 2330-2380 mg; about 2340-2390 mg; about 2350-2400 mg; about 1-4000 mg; about 1-1000 mg; about 10-1000 mg; about 50-1000 mg; about 10-600 mg; about 40-600 mg; about 50-600 mg; about 40-400 mg; about 50-200 mg; about 200-240 mg; about 240-280 mg; about 280-320 mg; about 320-360 mg; about 360-400 mg; about 400-450 mg; about 450-500 mg; about 500-600 mg; about 250-350 mg; about 100-600 mg; about 40-2000 mg; about 40-800 mg; about 100-900 mg; about 100-800 mg; about 40-1000 mg; about 50-1000 mg; about 100-1000 mg; or any monthly dose in a range bounded by, or between, any of these values.

A monthly dose of meloxicam may be given as a single dose, or as two or more individual doses administered during the month. In some embodiments, the monthly dose is administered bi-weekly in 2 or 3 divided doses. In some embodiments, the monthly dose is administered weekly in 4 or 5 divided doses. In some embodiments, the monthly dose is administered daily in 28 to 31 divided doses, or in 56 to 62 divided doses or more. In some embodiments, the monthly dose is administered in 5 to 15 individual doses during the month. The monthly dose may be administered for only 1 month, or may be repeatedly administered for 2, 3, 4, 5, 6, or more months.

In some embodiments, the daily dose of rizatriptan is about 0.5-100 mg, about 5-50 mg, about 1-10 mg, about 10-20 mg, about 20-30 mg, about 30-40 mg, about 40-50 mg, about 1-5 mg, about 1-6 mg, about 2-7 mg, about 3-8 mg, about 4-9 mg, about 5-10 mg, about 6-11 mg, about 7-12 mg, about 8-13 mg, about 9-14 mg, about 10-15 mg, about 11-16 mg, about 12-17 mg, about 13-18 mg, about 14-19 mg, about 15-20 mg, about 16-21 mg, about 17-22 mg, about 18-23 mg, about 19-24 mg, about 20-25 mg, about 21-26 mg, about 22-27 mg, about 23-28 mg, about 24-29 mg, about 25-30 mg, about 26-31 mg, about 27-32 mg, about 28-33 mg, about 29-34 mg, about 30-35 mg, about 31-36 mg, about 32-37 mg, about 33-38 mg, about 34-39 mg, about 35-40 mg, about 36-41 mg, about 37-42 mg, about 38-43 mg, about 39-44 mg, about 40-45 mg, about 41-46 mg, about 42-47 mg, about 43-48 mg, about 44-49 mg, about 45-50 mg, about 46-51 mg, about 47-52 mg, about 48-53 mg, about 49-54 mg, about 50-55 mg, or any amount in a range bounded by any of these values. The daily dose may be given as a single dose, given once a day, or may be given in 2, 3, 4, or more divided doses during a day.

In some embodiments, the weekly dose of rizatriptan is about 14000 mg; about 10-400 mg, about 50-250 mg, about 1-500 mg; about 10-250 mg; about 100-300 mg; about 10-100 mg; about 10-150 mg; about 10-300 mg; about 20-150 mg; about 20-60 mg; about 30-70 mg; about 40-60 mg; about 50-70 mg; about 70-90 mg; about 90-110 mg; about 50 mg; about 55 mg; about 100-150 mg; about 30-100 mg; about 1-20 mg; about 1-10 mg; about 2-10 mg; about 2-5 mg; about 540 mg; about 1-50 mg; about 10-60 mg; about 20-70 mg; about 30-80 mg; how about 40-90 mg; about 50-100 mg; about 60410 mg; about 70420 mg; about 80-130 mg; about 90-140 mg; about 100450 mg; about 110-160 mg; about 120-170 mg; about 130-180 mg; about 140490 mg; about 150-200 mg; about 160-210 mg; about 170-220 mg; about 180-230 mg; about 190-240 mg; about 200-250 mg; about 210-260 mg; about 220-270 mg; about 230-280 mg; about 240-290 mg; about 250-300 mg; about 260-310 mg; about 270-320 mg; about 280-330 mg; about 290-340 mg; about 300-350 mg; about 310-360 mg; about 320-370 mg; about 330-380 mg; about 340-390 mg; about 350-400 mg; or any amount in a range bounded by, or between, any of these values. The weekly dose may be given as a single dose, given once a week, or may be given in 2, 3, 4, 5, 6, or 7 individual doses during a week.

In some embodiments, the monthly dose of rizatriptan, or a total dose administered within a period of a month, is about 5000 mg or less; about 4000 mg or less; about 3000 mg or less; about 2000 mg or less; about 1000 mg or less; about 700 mg or less; about 600 mg or less; about 1-4000 mg; about 1-1000 mg; about 10-1000 mg; about 50-1000 mg; about 10-600 mg; about 40-600 mg; about 50-600 mg; about 150-2400 mg, about 150-200 mg; about 160-210 mg; about 170-220 mg; about 180-230 mg; about 190-240 mg; about 200-250 mg; about 210-260 mg; about 220-270 mg; about 230-280 mg; about 240-290 mg; about 250-300 mg; about 260-310 mg; about 270-320 mg; about 280-330 mg; about 290-340 mg; about 300-350 mg; about 310-360 mg; about 320-370 mg; about 330-380 mg; about 340-390 mg; about 350-400 mg; about 360-410 mg; about 370-420 mg; about 380-430 mg; about 390-440 mg; about 400-450 mg; about 410-460 mg; about 420-470 mg; about 430-480 mg; about 440-490 mg; about 450-500 mg; about 460-510 mg; about 470-520 mg; about 480-530 mg; about 490-540 mg; about 500-550 mg; about 510-560 mg; about 520-570 mg; about 530-580 mg; about 540-590 mg; about 550-600 mg; about 560-610 mg; about 570-620 mg; about 580-630 mg; about 590-640 mg; about 600-650 mg; about 610-660 mg; about 620-670 mg; about 630-680 mg; about 640-690 mg; about 650-700 mg; about 660-710 mg; about 670-720 mg; about 680-730 mg; about 690-740 mg; about 700-750 mg; about 710-760 mg; about 720-770 mg; about 730-780 mg; about 740-790 mg; about 750-800 mg; about 760-810 mg; about 770-820 mg; about 780-830 mg; about 790-840 mg; about 800-850 mg; about 810-860 mg; about 820-870 mg; about 830-880 mg; about 840-890 mg; about 850-900 mg; about 860-910 mg; about 870-920 mg; about 880-930 mg; about 890-940 mg; about 900-950 mg; about 910-960 mg; about 920-970 mg; about 930-980 mg; about 940-990 mg; about 950-1000 mg; about 960-1010 mg; about 970-1020 mg; about 980-1030 mg; about 990-1040 mg; about 1000-1050 mg; about 1010-1060 mg; about 1020-1070 mg; about 1030-1080 mg; about 1040-1090 mg; about 1050-1100 mg; about 1060-1110 mg; about 1070-1120 mg; about 1080-1130 mg; about 1090-1140 mg; about 1100-1150 mg; about 1110-1160 mg; about 1120-1170 mg; about 1130-1180 mg; about 1140-1190 mg; about 1150-1200 mg; about 1160-1210 mg; about 1170-1220 mg; about 1180-1230 mg; about 1190-1240 mg; about 1200-1250 mg; about 1210-1260 mg; about 1220-1270 mg; about 1230-1280 mg; about 1240-1290 mg; about 1250-1300 mg; about 1260-1310 mg; about 1270-1320 mg; about 1280-1330 mg; about 1290-1340 mg; about 1300-1350 mg; about 1310-1360 mg; about 1320-1370 mg; about 1330-1380 mg; about 1340-1390 mg; about 1350-1400 mg; about 1360-1410 mg; about 1370-1420 mg; about 1380-1430 mg; about 1390-1440 mg; about 1400-1450 mg; about 1410-1460 mg; about 1420-1470 mg; about 1430-1480 mg; about 1440-1490 mg; about 1450-1500 mg; about 1460-1510 mg; about 1470-1520 mg; about 1480-1530 mg; about 1490-1540 mg; about 1500-1550 mg; about 1510-1560 mg; about 1520-1570 mg; about 1530-1580 mg; about 1540-1590 mg; about 1550-1600 mg; about 1560-1610 mg; about 1570-1620 mg; about 1580-1630 mg; about 1590-1640 mg; about 1600-1650 mg; about 1610-1660 mg; about 1620-1670 mg; about 1630-1680 mg; about 1640-1690 mg; about 1650-1700 mg; about 1660-1710 mg; about 1670-1720 mg; about 1680-1730 mg; about 1690-1740 mg; about 1700-1750 mg; about 1710-1760 mg; about 1720-1770 mg; about 1730-1780 mg; about 1740-1790 mg; about 1750-1800 mg; about 1760-1810 mg; about 1770-1820 mg; about 1780-1830 mg; about 1790-1840 mg; about 1800-1850 mg; about 1810-1860 mg; about 1820-1870 mg; about 1830-1880 mg; about 1840-1890 mg; about 1850-1900 mg; about 1860-1910 mg; about 1870-1920 mg; about 1880-1930 mg; about 1890-1940 mg; about 1900-1950 mg; about 1910-1960 mg; about 1920-1970 mg; about 1930-1980 mg; about 1940-1990 mg; about 1950-2000 mg; about 1960-2010 mg; about 1970-2020 mg; about 1980-2030 mg; about 1990-2040 mg; about 2000-2050 mg; about 2010-2060 mg; about 2020-2070 mg; about 2030-2080 mg; about 2040-2090 mg; about 2050-2100 mg; about 2060-2110 mg; about 2070-2120 mg; about 2080-2130 mg; about 2090-2140 mg; about 2100-2150 mg; about 2110-2160 mg; about 2120-2170 mg; about 2130-2180 mg; about 2140-2190 mg; about 2150-2200 mg; about 2160-2210 mg; about 2170-2220 mg; about 2180-2230 mg; about 2190-2240 mg; about 2200-2250 mg; about 2210-2260 mg; about 2220-2270 mg; about 2230-2280 mg; about 2240-2290 mg; about 2250-2300 mg; about 2260-2310 mg; about 2270-2320 mg; about 2280-2330 mg; about 2290-2340 mg; about 2300-2350 mg; about 2310-2360 mg; about 2320-2370 mg; about 2330-2380 mg; about 2340-2390 mg; about 2350-2400 mg; about 40-400 mg; about 50-200 mg; about 200-240 mg; about 240-280 mg; about 280-320 mg; about 320-360 mg; about 360-400 mg; about 400-450 mg; about 450-500 mg; about 500-600 mg; about 250-350 mg; about 100-600 mg; about 40-2000 mg; about 40-800 mg; about 100-900 mg; about 100-800 mg; about 40-1000 mg; about 50-1000 mg; about 100-1000 mg; about 10-80 mg; about 10-40 mg; about 20-30 mg; or any monthly dose in a range bounded by, or between, any of these values. A monthly dose of rizatriptan may be given as a single dose, or as two or more individual doses administered during the month. In some embodiments, the monthly dose is administered bi-weekly in 2 or 3 divided doses. In some embodiments, the monthly dose is administered weekly in 4 or 5 divided doses. In some embodiments, the monthly dose is administered daily in 28 to 31 divided doses, or in 56 to 62 divided doses or more. In some embodiments, the monthly dose is administered in 5 to 15 individual doses during the month. The monthly dose may be administered for only 1 month, or may be repeatedly administered for 2, 3, 4, 5, 6, or more months.

In other embodiments, the subject combination may be administered weekly for about one, two, three, four, or more consecutive weeks, every other week or bi-weekly, or once every three weeks. This regimen may be repeated once weekly, twice in a month, three times in a month, once monthly, once every two months, once every three months, or as directed by a medical professional.

Any reference to $T_{max}$, $C_{max}$, AUC, or any other pharmacokinetic parameter should be understood to include an average, mean, or median value in human beings, such as human patients or human subjects.

The subject combination may be administered in an amount and manner intended to target therapeutically effective plasma concentrations. For example, an area under the plasma concentration curve (AUC) of meloxicam, such as a median, mean, or average AUC of meloxicam in human beings, of about 1-150 μg·hr/mL may be targeted, such as about 10-30 μg·hr/mL; about 20-40 μg·hr/mL; about 30-50 μg·hr/mL; about 40-60 μg·hr/mL; about 50-70 μg·hr/mL; about 60-80 μg·hr/mL; about 70-90 μg·hr/mL; about 80-100 μg·hr/mL; about 10-100 μg·hr/mL; about 50-150 μg·hr/mL; about 25-125 μg·hr/mL; about 75-150 μg·hr/mL; about 20-50 μg·hr/mL; about 40-70 μg·hr/mL; about 60-90 μg·hr/mL; about 80-110 μg·hr/mL; about 100-130 μg·hr/mL; about 120-150 μg·hr/mL; about 100-150 μg·hr/mL; about 20-30 μg·hr/mL; about 30-40 μg·hr/mL; about 40-50 μg·hr/mL; about 50-60 μg·hr/mL; about 20-25 μg·hr/mL, about 25-30 μg·hr/mL, about 30-35 μg·hr/mL, about 35-40 μg·hr/mL, about 40-45 μg·hr/mL, about 45-50 μg·hr/mL, or any AUC in a range bounded by, or between, any of these values.

Unless otherwise indicated, the AUC refers to the AUC calculated to the last measured concentration ($AUC_{0-t}$), such as, over a period of 6 hours ($AUC_{0-6}$), over a period of 12 hours ($AUC_{0-12}$), over a period of 24 hours ($AUC_{0-24}$), or extrapolated to infinity ($AUC_{0-inf}$).

In Example 1 below, the $AUC_{0-24}$ of meloxicam in human beings for an oral dosage form containing sodium bicarbonate and sulfobutylether β-cyclodextrin (SBEβCD) was about 27 μg·hr/mL. This dosage form contained 15 mg of meloxicam.

The 15 mg IV and intramuscular doses also provide an $AUC_{0-24}$ of meloxicam in human beings that is about 27 μg·hr/mL. The AUC of meloxicam is believed to be approximately dose proportional. So for this oral dosage form, or for an IV or intramuscular dosage form, a meloxicam dose of, for example, approximately 17 mg to about 30 mg would be expected to result in an $AUC_{0-24}$ of meloxicam of about 30-50 μg·hr/mL.

For some acute pain conditions, such as migraine and other types of headache, the AUC for a short period after oral administration, such as an AUC measured over 6 hours (or $AUC_{0-6}$), may be of particular interest, e.g. for quick pain relief. For example, some dosage forms may result in an $AUC_{0-6}$ of meloxicam, such as a median, mean, or average $AUC_{0-6}$ of meloxicam in human beings, that is at least about 5 μg·hr/mL (or 5,000 ng·hr/mL); at least about 6 μg·hr/mL (or 6,000 ng·hr/mL); at least about 7 μg·hr/mL (or 7,000 ng·hr/mL); at least about 8 μg·hr/mL (or 8,000 ng·hr/mL); at least about 9 μg·hr/mL (or 9,000 ng·hr/mL); about 6-10 μg·hr/mL; about 7-11 μg·hr/mL; about 8-12 μg·hr/mL; about 9-13 μg·hr/mL; about 10-14 μg·hr/mL; or any $AUC_{0-6}$ in a range bounded by, or between, any of these values.

In some embodiments, the subject combination is administered in a manner that results in a $C_{max}$ of meloxicam, such as a median, mean, or average $C_{max}$ of meloxicam in human beings, of about 10-2500 ng/mL; about 100-2250 ng/mL; about 500-2000 ng/mL; about 1000-2500 ng/mL; about 1000-2000 ng/mL; about 100-900 ng/mL; about 750-1500 ng/mL; about 1250-2000 ng/mL; about 1500-2300 ng/mL; about 800-1200 ng/mL; about 1900-2400 ng/mL; about 50-500 ng/mL; about 400-950 ng/mL; about 900-1500 ng/mL; about 1100-2200 ng/mL; about 1300-1600 ng/mL; about 1200-1500 ng/mL; about 1400-2100 ng/mL; about 1500-1900 ng/mL; about 1600-2100 ng/mL; about 1700-2000 ng/mL; about 1900-2500 ng/mL; about 1500-1700 ng/mL; about 1600-1800 ng/mL; about 1700-1900 ng/mL; about 1800-2000 ng/mL; about 1900-2100 ng/mL; about 2000-2200 ng/mL; about 2100-2300 ng/mL; about 2200-2400 ng/mL; about 2300-2500 ng/mL; about 2500-3000 ng/mL; at least about 1400 ng/mL; at least about 1500 ng/mL; at least about 1600 ng/mL; at least about 1700 ng/mL; at least about 1800 ng/mL; at least about 1900 ng/mL; at least about 2000 ng/mL; at least about 2100 ng/mL; at least about 2200 ng/mL; at least about 2300 ng/mL; at least about 2400 ng/mL; at least about 2500 ng/mL; or any $C_{max}$ in a range bounded by, or between, any of these values.

The methods described herein relate to administration of the subject combination in a human being in a manner that results in a relatively short $T_{max}$, such as a $T_{max}$ within about 10 minutes; within about 20 minutes; within about 30 minutes; within about 40 minutes; within about 50 minutes; within about 60 minutes; within about 70 minutes; within about 80 minutes; within about 90 minutes; within about 100 minutes; within about 110 minutes; within about 120 minutes; within about 180 minutes; about 10-30 minutes; about 20-40 minutes, about 30-50 minutes, about 40-60 minutes; about 50-70 minutes; about 60-90 minutes; about 70-100 minutes; about 80-110 minutes; about 90-120 minutes; or any $T_{max}$ in a range bounded by, or between, any of these values after administration of the subject combination.

In some embodiments, the subject combination is administered in a manner such that a time to half-maximal plasma concentration of meloxicam, such as a median, mean, or average time to half-maximal plasma concentration in human beings, that is less than about 5 minutes; less than about 10 minutes; less than about 15 minutes; less than about 20 minutes; less than about 25 minutes; less than about 30 minutes; less than about 35 minutes; less than about 40 minutes; less than about 45 minutes; less than about 50 minutes; less than about 55 minutes; less than about 60 minutes; less than about 90 minutes; about 5-15 minutes; about 10-20 minutes, about 15-25 minutes, about 20-30 minutes; about 25-35 minutes; about 30-45 minutes; about 35-50 minutes; about 40-55 minutes; about 45-60 minutes; about 0.5-5 hours; or any time in a range bounded by any of these values.

For example, a method described herein may reduce the $T_{max}$ of rizatriptan, such as a median, mean, or average $T_{max}$ of rizatriptan in human beings. In some embodiments, the method may include treating a patient to achieve the $T_{max}$ of rizatriptan in the patient within about 60 minutes; within about 70 minutes; within about 80 minutes; within about 90 minutes; within about 100 minutes; within about 110 minutes; within about 2 hours; within about 3 hours; within about 4 hours; about 10-30 minutes; about 20-40 minutes; about 30-50 minutes; about 40-60 minutes; about 50-70 minutes; about 60-80 minutes; about 70-90 minutes; about 0.1-1 hour; about 0.1-0.5 hours; about 0.5-1 hour; about 1-10 h; about 2-9 h; about 3-7 h; about 4-6 h; about 1-5 h; about 2-7 h; about 3-8 h; about 4-9 h; about 1-4 h; about 2-5 h; about 3-6 h; about 4-7 h; about 5-8 h; about 6-9 h; about 7-10 h; or any $T_{max}$ in a range bounded by, or between, any of these values after administration of the subject combination.

The oral dosage form of Example 1 below gave a $T_{max}$ of meloxicam of approximately 30 minutes. The $T_{max}$ of intravenous meloxicam is approximately 30 minutes for an infusion or 3 minutes for a bolus. The $T_{max}$ of intramuscular meloxicam is approximately 60-84 minutes.

In some embodiments, a subject combination may be administered in a manner that results in a plasma concentration of meloxicam, such as a median, mean, or average plasma concentration of meloxicam in human beings, at 12 hours that is about 0.01-0.5 μg/mL; about 0.5-0.7 μg/mL; about 0.6-0.8 μg/mL; about 0.7-0.9 μg/mL; about 0.8-1 μg/mL; about 0.01-1 μg/mL; about 0.9-1.1 μg/mL; about 1-1.2 μg/mL; about 1.1-1.3 μg/mL; about 1.2-1.4 μg/mL; about 1.3-1.5 μg/mL; about 1-1.5 μg/mL; about 1.4-1.6 μg/mL; about 1.5-1.7 μg/mL; about 1.6-1.8 μg/mL; about 1.7-1.9 μg/mL; about 1.8-2 μg/mL; about 1.5-2 μg/mL;

about 1.9-2.1 µg/mL; about 2-2.2 µg/mL; about 2.1-2.3 µg/mL; about 2.2-2.4 µg/mL; about 2.3-2.5 µg/mL; about 2-2.5 µg/mL; about 2.4-2.6 µg/mL; about 2.5-2.7 µg/mL; about 2.6-2.8 µg/mL; about 2.7-2.9 µg/mL; about 2.8-3 µg/mL; about 2.5-3 µg/mL; about 2.9-3.1 µg/mL; about 3-3.2 µg/mL; about 3.1-3.3 µg/mL; about 3.2-3.4 µg/mL; about 3.3-3.5 µg/mL; about 3-3.5 µg/mL; about 3.4-3.6 µg/mL; about 3.5-3.7 µg/mL; about 3.6-3.8 µg/mL; about 3.7-3.9 µg/mL; about 3.8-4 µg/mL; about 3.5-4 µg/mL; or any plasma concentration of meloxicam at 12 hours in a range bounded by, or between, any of these values.

In some embodiments, meloxicam is administered at a dose that results in a meloxicam average plasma level (such as a $C_{ave}$, or average plasma level) of about 0.01-0.5 µg/mL; about 0.5-0.7 µg/mL; about 0.6-0.8 µg/mL; about 0.7-0.9 µg/mL; about 0.8-1 µg/mL; about 0.01-1 µg/mL; about 0.9-1.1 µg/mL; about 1-1.2 µg/mL; about 1.1-1.3 µg/mL; about 1.2-1.4 µg/mL; about 1.3-1.5 µg/mL; about 1.4-1.6 µg/mL; about 1.5-1.7 µg/mL; about 1.6-1.8 µg/mL; about 1.7-1.9 µg/mL; about 1.8-2 µg/mL; about 1-2 µg/mL; about 0.01-3 µg/mL; about 1.9-2.1 µg/mL; about 2-2.2 µg/mL; about 2.1-2.3 µg/mL; about 2.2-2.4 µg/mL; about 2.3-2.5 µg/mL; about 2.4-2.6 µg/mL; about 2.5-2.7 µg/mL; about 2.6-2.8 µg/mL; about 2.7-2.9 µg/mL; about 2.8-3 µg/mL; about 2-3 µg/mL; about 2.9-3.1 µg/mL; about 3-3.2 µg/mL; about 3.1-3.3 µg/mL; about 3.2-3.4 µg/mL; about 3.3-3.5 µg/mL; about 3.4-3.6 µg/mL; about 3.5-3.7 µg/mL; about 3.6-3.8 µg/mL; about 3.7-3.9 µg/mL; about 3.8-4 µg/mL; about 3-4 µg/mL; about 2-4 µg/mL; about 0.01-4 µg/mL; about 0.1-20 µg/mL; about 0.5-15 µg/mL; about 0.5-10 µg/mL; about 5-15 µg/mL; about 10-20 µg/mL; about 7.5-15 µg/mL; about 2-10 µg/m L; about 1-8 µg/mL; about 1-6 µg/mL; about 1-2 µg/mL; about 0.5-3.5 µg/mL; about 0.5-7 µg/m L; about 12-20 µg/mL; about 8-12 µg/mL; about 1-4 µg/mL; about 4-7 µg/mL; about 7-11 µg/mL; about 11-15 µg/mL; about 15-19 µg/mL; about 16-20 µg/mL; or any meloxicam average plasma level in a range bounded by, or between, any of these values.

In some embodiments, a dosage form containing meloxicam, rizatriptan, or both, may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, coated tablets, troches, capsules, elixirs, dispersions, suspensions, solutions, syrups, wafers, patches, and the like.

Tablets, troches, pills, capsules and the like may also contain one or more of the following: a binder such as gum tragacanth, acacia, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the unit dosage form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non-toxic in the amounts employed.

Some single dosage forms contain both meloxicam and rizatriptan may further contain, a cyclodextrin which may be complexed with meloxicam, and a bicarbonate. In addition, some dosage forms may contain excipients such as microcrystalline cellulose (e.g. about 1-20%), starch (e.g. about 1-10%), fumed silica (e.g. 0.1-10%), polyvinylpyrrolidone (e.g. about 1-10%), and/or magnesium stearate (e.g. about 0.1-10%).

Some compositions or dosage forms may be a liquid, or may comprise a solid phase dispersed in a liquid.

Example 1

A bilayer tablet containing 1) an inclusion complex of SBEβCD with meloxicam, prepared as described below, and 2) sodium bicarbonate was prepared (SBEβCD-Meloxicam/Bicarbonate). The first layer contained an inclusion complex of 15 mg meloxicam and 100 mg SBEβCD, and 100 mg of sodium bicarbonate. The second layer contained 40 mg of esomeprazole and 400 mg of sodium bicarbonate.

A total of 20 human subjects were randomly assigned in a 1:1 ratio to treatment with the SBEβCD-Meloxicam/Bicarbonate tablets described above or Mobic® tablets (15 mg meloxicam), once daily for 6 days under fasting conditions.

On the first day of dosing, plasma samples were collected for concentration analysis of meloxicam at several time points. Concentrations of meloxicam were determined using LC-MS/MS. Pharmacokinetic parameters were calculated. The results are depicted in FIG. 1.

The median $T_{max}$ for meloxicam, the trial's primary endpoint, was 9 times faster for the SBEβCD-Meloxicam/Bicarbonate tablets as compared to Mobic® (0.5 hour versus 4.5 hours respectively, p<0.0001).

The SBEβCD-Meloxicam/Bicarbonate tablets also demonstrated higher mean maximum plasma concentration ($C_{max}$) (p=0.0018), faster time to therapeutic plasma concentration (p<0.0001), and faster time to half-maximal plasma concentration (p<0.0001) as compared to Mobic®.

Meloxicam in the form of meloxicam/cyclodextrin inclusion complexes was used in the tablets containing meloxicam and cyclodextrin. The inclusion complexes were formed by mixing meloxicam and cyclodextrin in an aqueous pH-adjusted solution. The pH of the solution was adjusted using buffering agents. The resulting soluble meloxicam/cyclodextrin inclusion complexes were then spray dried. This spray-dried dispersion was used in the manufacture of the tablets containing cyclodextrin.

Example 2

A monolayer tablet containing 1) the inclusion complex of SBEβCD with meloxicam; 2) rizatriptan; and 3) sodium bicarbonate was prepared (SBEβCD-Meloxicam/rizatriptan/Bicarbonate). The monolayer tablet contained 20 mg of meloxicam, 10 mg of rizatriptan, and 500 mg of sodium bicarbonate. The inclusion complex was the same as the inclusion complex of Example 1.

Dissolution testing of the tablets in acidic medium (chosen to simulate gastric conditions) was performed by placing the tablets in a 0.01 N HCl solution, at an agitation rate of 75 RPM, and vessel temperature of approximately 37° C. The results are presented in Table 7. Results at various time points (0, 15, 30, 45, 60, 90, and 120 minutes) are presented as percent (%) of meloxicam, and percent (%) of rizatriptan dissolved.

TABLE 7

| Dissolution Results | | | | | | | |
|---|---|---|---|---|---|---|---|
| Time-point (minutes) | 0 min | 15 min | 30 min | 45 min | 60 min | 90 min | 120 min |
| Rizatriptan | 0% | 89% | 102% | 103% | 103% | 103% | 103% |
| Meloxicam | 0% | 79% | 92% | 93% | 93% | 93% | 94% |

As shown in Table 7, the dissolution results of the tablets in Example 2 are very similar to the dissolution result of Example 1. Therefore, we expect the pharmacokinetic properties, including bioavailability, $T_{max}$, etc., of the tablets in Example 2 to be similar to those described in Example 1 and FIG. 1.

Example 3

The monolayer tablet of Example 2 was administered to six human subjects. On the first day of dosing, plasma samples were collected for concentration analysis of rizatriptan at several time points. Concentrations of rizatriptan and meloxicam were determined using LC-MS/MS. Pharmacokinetic parameters were calculated. The results for meloxicam were comparable to those reported for the bilayer dosage form of Example 1. The median $T_{max}$ of rizatriptan was 0.75 hours and the mean $C_{max}$ of rizatriptan was 20.710 ng/mL. By comparison, the reported $T_{max}$ of the commercial rizatriptan dosage form, Maxalt®, is 1.0-1.5 hours.

Unless otherwise indicated, all numbers expressing quantities of ingredients, properties such as molecular weight, reaction conditions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

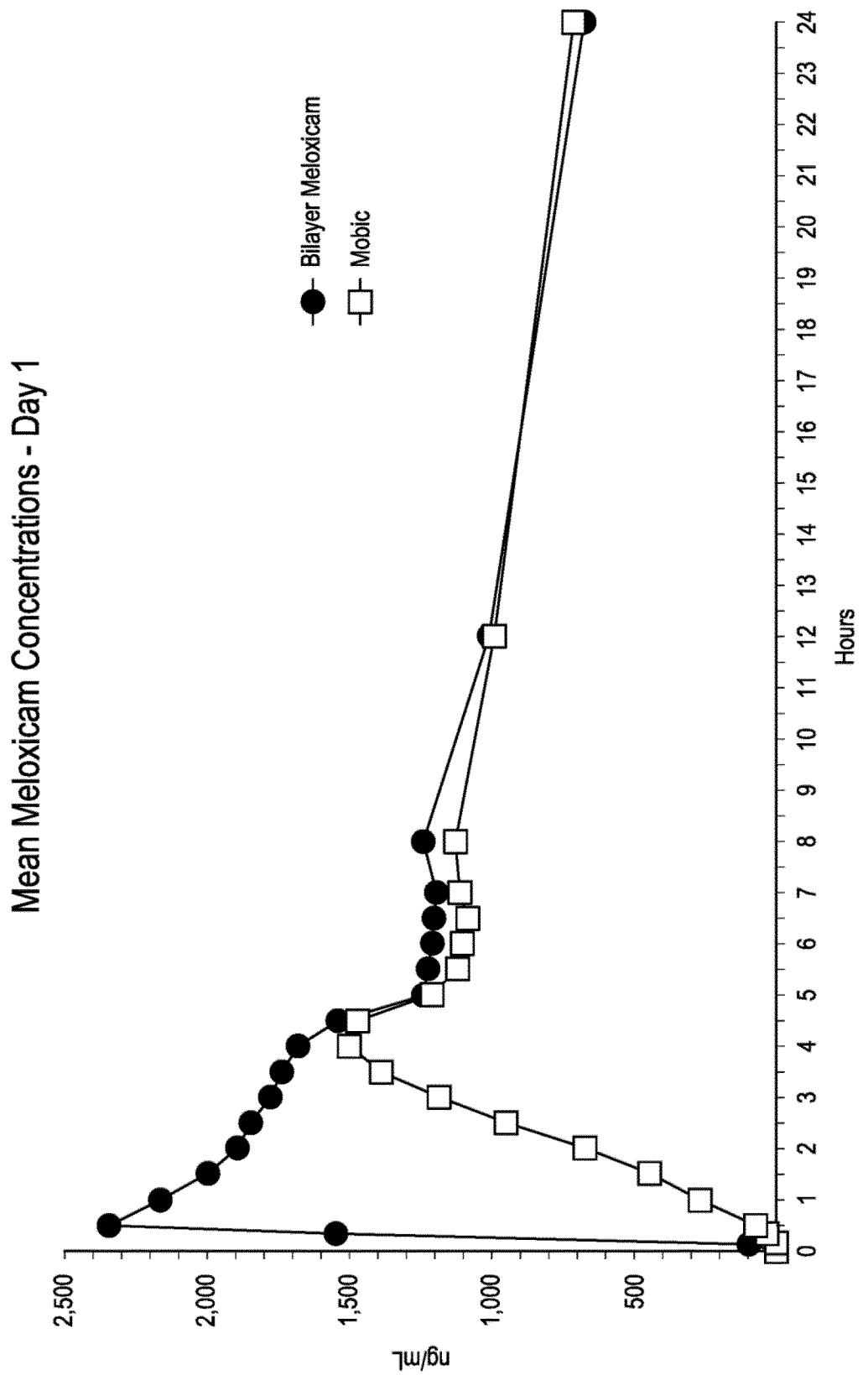

The invention claimed is:

1. A method of treating migraine, comprising administering a meloxicam and about 8 mg to about 13 mg of a rizatriptan, based upon the weight of the free base form of rizatriptan, to a human being who is suffering from an acute attack of migraine pain or migraine aura, wherein the meloxicam and the rizatriptan are administered within about 30 minutes of one another, wherein administering the meloxicam to the human being results in a $T_{max}$ of meloxicam of 110 minutes or less, and an $AUC_{0-24}$ of meloxicam of about 30 μg·hr/mL to about 50 μg·hr/mL, and wherein two hours after the meloxicam and the rizatriptan are administered, the human being experiences greater relief from nausea than the human being would have experienced two hours after receiving the same amount of the meloxicam without the rizatriptan.

2. The method of claim 1, wherein the rizatriptan is administered in a salt form in an amount that is a molar equivalent to about 10 mg of the free base form of rizatriptan.

3. The method of claim 2, wherein the rizatriptan is present as rizatriptan benzoate.

4. The method of claim 1, wherein about 15 mg to about 25 mg of the meloxicam is administered to the human being.

5. The method of claim 1, wherein about 20 mg of the meloxicam is administered to the human being.

6. The method of claim 1, wherein the human being has a history of inadequate response to prior migraine treatments.

7. The method of claim 6, wherein the rizatriptan is administered in a salt form in an amount that is a molar equivalent to about 10 mg of the free base form of rizatriptan.

8. The method of claim 6, wherein about 15 mg to about 25 mg of the meloxicam is administered to the human being.

9. The method of claim 7, wherein about 20 mg of the meloxicam is administered to the human being.

10. The method of claim 1, wherein the meloxicam and the rizatriptan are administered simultaneously, and wherein two hours after the meloxicam and the rizatriptan are administered, the human being experiences greater pain relief than the human being would have experienced two hours after receiving the same amount of the meloxicam without the rizatriptan.

11. The method of claim 10, wherein the rizatriptan is administered in a salt form in an amount that is a molar equivalent to about 10 mg of the free base form of rizatriptan.

12. The method of claim 10, wherein about 15 mg to about 25 mg of the meloxicam is administered to the human being.

13. The method of claim 11, wherein about 20 mg of the meloxicam is administered to the human being.

14. The method of claim 1, wherein the meloxicam and the rizatriptan are administered simultaneously, and wherein two hours after the meloxicam and the rizatriptan are administered, the human being experiences greater pain relief than the human being would have experienced two hours after receiving the same amount of the rizatriptan without the meloxicam.

15. The method of claim 14, wherein the rizatriptan is administered in a salt form in an amount that is a molar equivalent to about 10 mg of the free base form of rizatriptan.

16. The method of claim 14, wherein about 15 mg to about 25 mg of the meloxicam is administered to the human being.

17. The method of claim 15, wherein about 20 mg of the meloxicam is administered to the human being.

18. The method of claim 1, wherein the meloxicam and the rizatriptan are administered simultaneously, and wherein two hours after the meloxicam and the rizatriptan are administered, the human being experiences greater relief from nausea than the human being would have experienced two hours after receiving the same amount of the meloxicam without the rizatriptan.

19. A method of treating migraine, comprising administering a meloxicam and about 8 mg to about 13 mg of a rizatriptan, based upon the weight of the free base form of rizatriptan, to a human being who is suffering from an acute attack of migraine pain or migraine aura, wherein the meloxicam and the rizatriptan are administered within about 30 minutes of one another, wherein administering the meloxicam to the human being results in a $T_{max}$ of meloxicam of 110 minutes or less, and an $AUC_{0-24}$ of meloxicam of about 30 µg·hr/mL to about 50 µg·hr/mL, and wherein two hours after the meloxicam and the rizatriptan are administered, the human being experiences greater relief from nausea than the human being would have experienced two hours after receiving the same amount of the rizatriptan without the meloxicam.

20. A method of treating migraine, comprising administering a meloxicam and about 8 mg to about 13 mg of a rizatriptan, based upon the weight of the free base form of rizatriptan, to a human being who is suffering from an acute attack of migraine pain or migraine aura, wherein the meloxicam and the rizatriptan are administered within about 30 minutes of one another, wherein administering the meloxicam to the human being results in a $T_{max}$ of meloxicam of 110 minutes or less, and an $AUC_{0-24}$ of meloxicam of about 30 µg·hr/mL to about 50 µg·hr/mL, and wherein two hours after the meloxicam and the rizatriptan are administered, the human being experiences greater relief from vomiting than the human being would have experienced two hours after receiving the same amount of the meloxicam without the rizatriptan.

21. A method of treating migraine, comprising administering a meloxicam and about 8 mg to about 13 mg of a rizatriptan, based upon the weight of the free base form of rizatriptan, to a human being who is suffering from an acute attack of migraine pain or migraine aura, wherein the meloxicam and the rizatriptan are administered within about 30 minutes of one another, wherein administering the meloxicam to the human being results in a $T_{max}$ of meloxicam of 110 minutes or less, and an $AUC_{0-24}$ of meloxicam of about 30 µg·hr/mL to about 50 µg·hr/mL, and wherein two hours after the meloxicam and the rizatriptan are administered, the human being experiences greater relief from vomiting than the human being would have experienced two hours after receiving the same amount of the rizatriptan without the meloxicam.

22. A method of treating migraine, comprising administering a meloxicam and about 8 mg to about 13 mg of a rizatriptan, based upon the weight of the free base form of rizatriptan, to a human being who is suffering from an acute attack of migraine pain or migraine aura, wherein the meloxicam and the rizatriptan are administered within about 30 minutes of one another, wherein administering the meloxicam to the human being results in a $T_{max}$ of meloxicam of 110 minutes or less, and an $AUC_{0-24}$ of meloxicam of about 30 µg·hr/mL to about 50 µg·hr/mL, and wherein two hours after the meloxicam and the rizatriptan are administered, the human being experiences greater relief from photophobia than the human being would have experienced two hours after receiving the same amount of the meloxicam without the rizatriptan.

23. A method of treating migraine, comprising administering a meloxicam and about 8 mg to about 13 mg of a rizatriptan, based upon the weight of the free base form of rizatriptan, to a human being who is suffering from an acute attack of migraine pain or migraine aura, wherein the meloxicam and the rizatriptan are administered within about 30 minutes of one another, wherein administering the meloxicam to the human being results in a $T_{max}$ of meloxicam of 110 minutes or less, and an $AUC_{0-24}$ of meloxicam of about 30 µg·hr/mL to about 50 µg·hr/mL, and wherein two hours after the meloxicam and the rizatriptan are administered, the human being experiences greater relief from photophobia than the human being would have experienced two hours after receiving the same amount of the rizatriptan without the meloxicam.

24. A method of treating migraine, comprising administering a meloxicam and about 8 mg to about 13 mg of a rizatriptan, based upon the weight of the free base form of rizatriptan, to a human being who is suffering from an acute attack of migraine pain or migraine aura, wherein the meloxicam and the rizatriptan are administered within about 30 minutes of one another, wherein administering the meloxicam to the human being results in a $T_{max}$ of meloxicam of 110 minutes or less, and an $AUC_{0-24}$ of meloxicam of about 30 µg·hr/mL to about 50 µg·hr/mL, and wherein two hours after the meloxicam and the rizatriptan are administered, the human being experiences greater relief from phonophobia than the human being would have experienced two hours after receiving the same amount of the meloxicam without the rizatriptan.

25. A method of treating migraine, comprising administering a meloxicam and about 8 mg to about 13 mg of a rizatriptan, based upon the weight of the free base form of rizatriptan, to a human being who is suffering from an acute attack of migraine pain or migraine aura, wherein the meloxicam and the rizatriptan are administered within about 30 minutes of one another, wherein administering the meloxicam to the human being results in a $T_{max}$ of meloxicam of 110 minutes or less, and an $AUC_{0-24}$ of meloxicam of about 30 µg·hr/mL to about 50 µg·hr/mL, and wherein two hours after the meloxicam and the rizatriptan are administered, the human being experiences greater relief from phonophobia than the human being would have experienced two hours after receiving the same amount of the rizatriptan without the meloxicam.

26. The method of claim 19, wherein the rizatriptan is administered in a salt form in an amount that is a molar equivalent to about 10 mg of the free base form of rizatriptan.

27. The method of claim 26, wherein the rizatriptan is present as rizatriptan benzoate.

28. The method of claim 19, wherein about 15 mg to about 25 mg of the meloxicam is administered to the human being.

29. The method of claim 19, wherein about 20 mg of the meloxicam is administered to the human being.

30. The method of claim 19, wherein the human being has a history of inadequate response to prior migraine treatments.

31. The method of claim 30, wherein the rizatriptan is administered in a salt form in an amount that is a molar equivalent to about 10 mg of the free base form of rizatriptan.

32. The method of claim 30, wherein about 15 mg to about 25 mg of the meloxicam is administered to the human being.

33. The method of claim 31, wherein about 20 mg of the meloxicam is administered to the human being.

34. The method of claim 19, wherein the meloxicam and the rizatriptan are administered simultaneously, and wherein two hours after the meloxicam and the rizatriptan are administered, the human being experiences greater relief from nausea than the human being would have experienced two hours after receiving the same amount of the meloxicam without the rizatriptan.

35. The method of claim 34, wherein the rizatriptan is administered in a salt form in an amount that is a molar equivalent to about 10 mg of the free base form of rizatriptan.

36. The method of claim 34, wherein about 15 mg to about 25 mg of the meloxicam is administered to the human being.

37. The method of claim 35, wherein about 20 mg of the meloxicam is administered to the human being.

38. The method of claim 19, wherein the meloxicam and the rizatriptan are administered simultaneously, and wherein two hours after the meloxicam and the rizatriptan are administered, the human being experiences greater relief from nausea than the human being would have experienced two hours after receiving the same amount of the rizatriptan without the meloxicam.

39. The method of claim 38, wherein the rizatriptan is administered in a salt form in an amount that is a molar equivalent to about 10 mg of the free base form of rizatriptan.

40. The method of claim 38, wherein about 15 mg to about 25 mg of the meloxicam is administered to the human being.

41. The method of claim 39, wherein about 20 mg of the meloxicam is administered to the human being.

42. The method of claim 20, wherein the meloxicam and the rizatriptan are administered simultaneously, and wherein two hours after the meloxicam and the rizatriptan are administered, the human being experiences greater relief from vomiting than the human being would have experienced two hours after receiving the same amount of the meloxicam without the rizatriptan.

43. The method of claim 21, wherein the meloxicam and the rizatriptan are administered simultaneously, and wherein two hours after the meloxicam and the rizatriptan are administered, the human being experiences greater relief from vomiting than the human being would have experienced two hours after receiving the same amount of the rizatriptan without the meloxicam.

44. The method of claim 22, wherein the meloxicam and the rizatriptan are administered simultaneously, and wherein two hours after the meloxicam and the rizatriptan are administered, the human being experiences greater relief from photophobia than the human being would have experienced two hours after receiving the same amount of the meloxicam without the rizatriptan.

45. The method of claim 23, wherein the meloxicam and the rizatriptan are administered simultaneously, and wherein two hours after the meloxicam and the rizatriptan are administered, the human being experiences greater relief from photophobia than the human being would have experienced two hours after receiving the same amount of the rizatriptan without the meloxicam.

46. The method of claim 24, wherein the meloxicam and the rizatriptan are administered simultaneously, and wherein two hours after the meloxicam and the rizatriptan are administered, the human being experiences greater relief from phonophobia than the human being would have experienced two hours after receiving the same amount of the meloxicam without the rizatriptan.

47. The method of claim 25, wherein the meloxicam and the rizatriptan are administered simultaneously, and wherein two hours after the meloxicam and the rizatriptan are administered, the human being experiences greater relief from phonophobia than the human being would have experienced two hours after receiving the same amount of the rizatriptan without the meloxicam.

* * * * *

UNITED STATES PATENT AND TRADEMARK OFFICE
CERTIFICATE OF CORRECTION

PATENT NO. : 10,688,102 B2
APPLICATION NO. : 16/513612
DATED : June 23, 2020
INVENTOR(S) : Herriot Tabuteau Page 1 of 2

It is certified that error appears in the above-identified patent and that said Letters Patent is hereby corrected as shown below:

In the Drawings

Please use the attached drawing as replacement for the figure.

Signed and Sealed this
Eighth Day of December, 2020

Andrei Iancu
*Director of the United States Patent and Trademark Office*